(12) United States Patent
Kheradvar et al.

(10) Patent No.: US 8,767,049 B2
(45) Date of Patent: Jul. 1, 2014

(54) MEMBRANE-DEFORMATION MAPPING TECHNIQUE

(75) Inventors: Arash Kheradvar, Blythewood, SC (US); Michael A. Sutton, Columbia, SC (US)

(73) Assignee: University of South Carolina, Columbia, SC (US)

(*) Notice: Subject to any disclaimer, the term of this patent is extended or adjusted under 35 U.S.C. 154(b) by 1099 days.

(21) Appl. No.: 12/506,521

(22) Filed: Jul. 21, 2009

(65) Prior Publication Data
US 2010/0016711 A1 Jan. 21, 2010

Related U.S. Application Data

(60) Provisional application No. 61/135,475, filed on Jul. 21, 2008.

(51) Int. Cl.
*H04N 13/02* (2006.01)
*G01J 5/04* (2006.01)

(52) U.S. Cl.
USPC .......................................... 348/47; 600/306

(58) Field of Classification Search
CPC .......... H04N 13/0239; H04N 13/0296; H04N 13/0055; H04N 2013/0081; G06T 7/0022; A61B 5/0059; A61B 5/441; A61B 5/442; A61B 5/445; A61B 5/444
USPC .......................................... 348/47; 382/128
See application file for complete search history.

(56) References Cited

U.S. PATENT DOCUMENTS

| | | | |
|---|---|---|---|
| 6,603,552 B1 * | 8/2003 | Cline et al. | 356/417 |
| 7,344,498 B1 * | 3/2008 | Doughty et al. | 600/306 |
| 7,922,764 B2 * | 4/2011 | Gordy et al. | 623/2.42 |

OTHER PUBLICATIONS

Gao, B.Z.; Hwang, N.H.C.; , "Bioprosthetic heart valve leaflet deformation monitored by double pulse stereo photogrammetry," [Engineering in Medicine and Biology, 1999. 21st Annual Conf. and the 1999 Annual Fall Meeting of the Biomedical Engineering Soc.] BMES/EMBS Conference, 1999. Proceedings of the First Joint, vol. 1, no., pp. 175 vol. 1, 1999 doi.*
Lee, M.K.; Holdsworth, D.W.; Fenster, A.; "Dynamic 3D computed tomography: non-invasive method for determination of the aortic dynamic elastic modulus," Engineering in Medicine and Biology Society, 2000. Proceedings of the 22nd Annual International Conference of the IEEE, vol. 1, no., pp. 661-664 vol. 1, 2000 doi: 10.1109/IEMBS.2000.900831.*
Gao, B.Z.; Hwang, N.H.C.; "Bioprosthetic heart valve leaflet deformation monitored by double pulse stereo photogrammetry," [Engineering in Medicine and Biology, 1999.21st Annual Conf. and the 1999 Annual Fall Meeting of the Biomedical Engineering Soc.] BMES/EMBS Conference, 1999. Proceedings of the First Joint, vol. 1, no., pp. 175 vol. 1, 1999 doi:1.*
Gao et al. "Bioprosthetic Heart Valve Leaflet Deformation Monitored by Double-Pulse Stereo Photogrammetry" , Annals of Biomedical engineering, vol. 30, 2000, pp. 11-18.

* cited by examiner

*Primary Examiner* — Sath V Perungavoor
*Assistant Examiner* — Howard D Brown, Jr.
(74) *Attorney, Agent, or Firm* — Dority & Manning, P.A.

(57) ABSTRACT

In accordance with one embodiment of the present disclosure, a method for deformation mapping of a tissue is provided. The method includes utilizing a device to measure transient three-dimensional deformations in a tissue sample. The device comprises a non-contacting, high-speed stereo imaging apparatus and a mechanism for digital image correlation. The method further includes identifying regions of the tissue that are prone to damage based upon the deformations.

10 Claims, 8 Drawing Sheets

MEMBRANE-DEFORMATION MAPPING TECHNIQUE

CROSS-REFERENCE TO RELATED APPLICATION

The present application is based on and claims priority to U.S. Provisional Application 61/135,475 having a filing date of Jul. 21, 2008, which is incorporated by reference herein.

BACKGROUND

Bioprosthetic heart valves (BHVs) are routinely used as replacements for diseased natural valves. BHVs have lower risks of thrombogenicity and superior hemodynamics, when compared to the mechanical valves. However, BHVs do not have favorable long-term durability, primarily due to early structural failure of the leaflets. Although a range of failure mechanisms have been proposed to explain observed leaflet failures, mechanical stress during valve operation plays a significant role in failure.

To date, prototype valve durability has been quantified using experimental equipment (e.g. Rowan Ash fatigue tester, Helmholtz-type accelerated durability tester) based on FDA/ANSI/AAMI/ISO durability guidelines, even though it has been shown that accelerated testing performed under current guidelines has an uncertain relationship with in-vivo conditions. Indeed, accurate assessment of valve durability in a non-contacting, timely manner is one of the most important unresolved issues in the basic research of artificial organs. Because accelerated fatigue testers cannot provide quantitative information related to dynamics of the leaflets, experimental results for BHVs must be assessed within the framework of existing experimental limitations.

Given the difficulty in quantifying the constitutive relationship for the highly nonlinear tissue leaflets in BHVs, a plausible approach that provides quantitative data essential for reliable model prediction of leaflet durability is to measure the true, three-dimensional, transient leaflet kinematics during the opening and closure of BHVs under conditions that are similar to those experienced by the human heart. Through direct measurements, the necessary response characteristics of the leaflets to physiologic pressure/flow conditions can be obtained. Furthermore, successful implementation of a non-contacting deformation measurement system can provide insight for development of a lab-based experiment capable of quantifying the constitutive response of thin non-linear membranes, such as the valve leaflet.

Thus, a need exists for a global methodology based on a non-contacting, image-based measurement method to evaluate the three-dimensional mechanical response of tissue membranes, such as the heart valve's leaflets, in response to a variety of physiologic loading conditions. In addition, it would be desirable to use digital image correlation combined with high-speed stereo imaging to measure the transient three-dimensional deformations of the tissue leaflets under a number of pulsatile flow conditions.

SUMMARY

In accordance with one embodiment of the present disclosure, a method for deformation mapping of a tissue is provided. The method includes utilizing a device to measure transient three-dimensional deformations in a tissue sample. The device comprises a non-contacting, high-speed stereo imaging apparatus and a mechanism for digital image correlation. The method further includes identifying regions of the tissue that are prone to damage based upon the deformations.

In another embodiment of the present disclosure, a device for deformation mapping a tissue is provided. The device includes a non-contacting, high-speed stereo imaging apparatus and a mechanism for digital image correlation. The high speed stereo imaging apparatus and the mechanism for digital image correlation are configured to measure transient three-dimensional deformations in a tissue sample.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which.

DETAILED DESCRIPTION

Figure 1A:
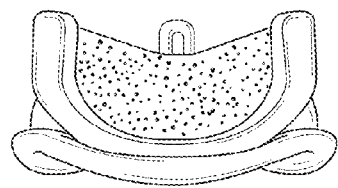
FIG. 1 illustrates (A) anterior leaflet of a bioprosthetic heart valve marked with a number of randomly distributed dots, (B) partly schematic of tissue leaflet deformation, measuring the deformation of vector R for each point on the leaflet would result in capturing the leaflet deformation, in accordance with certain embodiments of the present disclosure.

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

When implanted inside the heart, tissue valve prostheses experience a variety of failure modes, including mechanical rupture, cyclic degradation under fatigue conditions (e.g., cyclic bending strains) and local separation in the presence of highly concentrated membrane stresses. In particular, flexural stresses and associated deformations during valve opening and closure have been reported to play a considerable role in limiting long-term BHV durability. Additionally, leaflet failure can be associated with tissue calcification and loss of cusp extensibility. Besides calcification, ultrastructural disruption of the extracellular matrix (ECM), including type I collagen fibrils, has also been noted as a cause of failure. Even so, little is known about the molecular mechanisms whereby mechanical stress and deformation result in tissue deterioration.

Current tri-leaflet bioprostheses, regardless of the type of leaflet tissue (e.g. bovine pericardium, porcine leaflets, polyurethanes, etc.) have been found to fail frequently within the commissural region at the leaflet-stent attachments. Rupture of the leaflet usually starts at the cusp's free edge and subsequently propagates toward the stent resulting in separation of tissue from stent. A number of mechanisms can lead to leaflet failure under cyclic loading. For example, abrasion frequently occurs at the interface of leaflet and stent whereas cyclic bending strains commonly occurs either at the commissures when the valve is fully open or at the center of the leaflet when the valve is closing.

Accurate assessment of valve durability in a non-contacting, timely manner is one of the most important unresolved issues in the basic research of artificial organs. ISO 5840 for Cardiovascular Implants (Cardiac Valve Prostheses), incorporated by reference herein, prescribes guidelines for accelerated fatigue testing of valves as a widely accepted component in development of BHVs. However, varying degrees of success have been reported in obtaining a correlation between the defects observed in clinical cases and the failure modes observed during in-vitro accelerated fatigue tests. This is particularly true with regard to BHVs. As a result, a non-contacting method that can quantify the local variations in mechanical response of the leaflets, leading to the ability to predict potential future failure of a valve prior to clinical use through corresponding experimental measurements, can improve the quality of the heart valves and increase their functional durability. Such a method would also be most beneficial if it can assess every heart valve after production and prior to release in the market.

The present disclosure is directed to a global methodology based on a non-contacting, image-based measurement method to evaluate the three-dimensional mechanical response of tissue membranes, such as the BHV's leaflets, in response to a variety of pressure/flow conditions. In particular, the present disclosure utilizes 3D digital image correlation combined with high-speed stereo imaging to measure the transient three-dimensional deformations of the heart valve's leaflets under physiologic/pathologic flow conditions. This information results in identifying regions of a leaflet that incur large deformations and hence may be prone to damage within the period of valve function. Additionally, this methodology allows non-invasive evaluation of every heart valve prior to release for clinical use and can detect anomalous response (i.e., functionally defects) for leaflets operating under physiologic conditions that appear to be normal under current testing methods. In-vitro assessment of leaflet deformation under conditions similar to the human heart is a vital step to understand the mechanical properties of tissue leaflets made of biological materials within a heart valve.

The present disclosure further contemplates experimental approaches for estimating the constitutive response of thin non-linear membranes using a combination of the non-contacting deformation measurement system and mechanical loading devices, and a vision-based methodology for non-invasive, in-vivo assessment of natural heart valves that may include optical, ultrasound or other incident waves.

While in-vivo study of the mechanical characteristics of a bioprosthetic heart valve has previously been limited due to practical difficulties, computational investigations such as finite element analysis (FEA) are indirect methods that have been used to study the leaflet's dynamics. Computational approaches for predicting structural aspects of the valve response generally have not considered fluid-solid interactions, with many of the FEA predictions being difficult to validate in-vivo using available imaging technologies. Another model idealization that has been employed is to assume the functional form for the valve motion, an approximation that may decrease the accuracy of the model predictions.

Recently, an imaging technique has been introduced to quantify the in-surface, two-dimensional strain map of a valve leaflet. A non-contacting, structured, laser-light technique was utilized to project a matrix of 150-200 laser light-points on the leaflet surface. Since the projected pattern determines the current shape, but not the true motion of material point on the surface, the shape measurements were combined, extracted by tracking the motion of the projected dot pattern with a Lagrangian quadratic finite element method to determine the two-dimensional, in-surface strain tensor. Although this method is considered a non-contacting approach to study BHVs' mechanical behavior, the principal limitation of the approach is that the projected pattern method is confined to in-surface profile mapping, requiring integration with a computational model to analyze bending and wrinkling of leaflets.

Figure 1B:
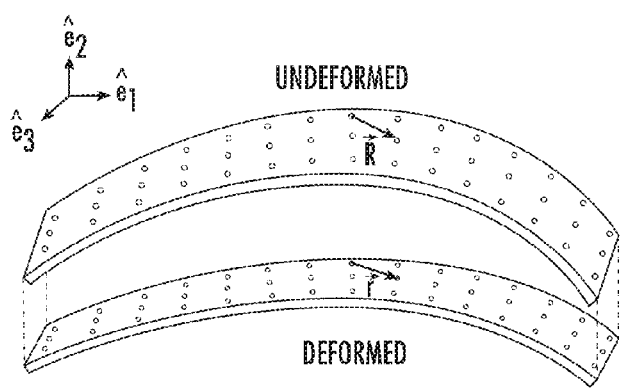
Figure 2A:
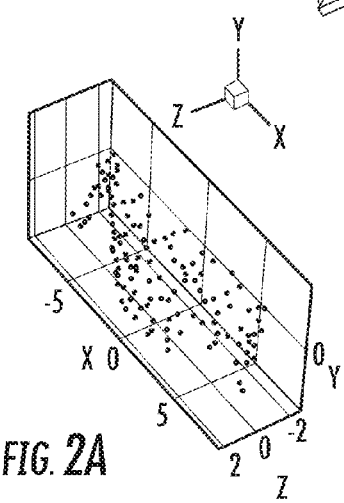
FIG. 2 illustrates (A) dot markers over the anterior leaflet of a bioprosthetic mitral valve captured as tracing particles; (B) strain field of the anterior leaflet of the mitral valve while opening under the effect of trans-mitral flow, in accordance with certain embodiments of the present disclosure.
Figure 2B:
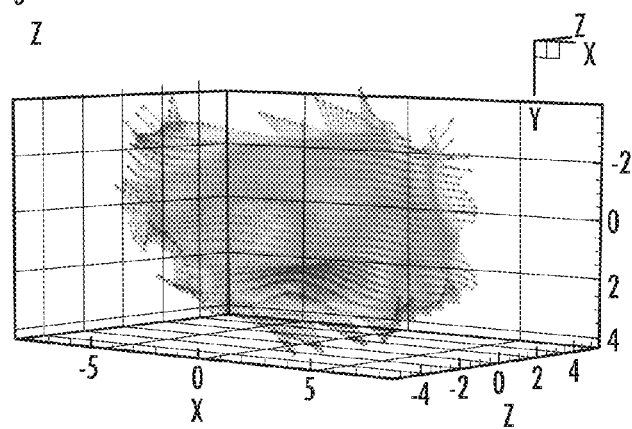

Previously, the present inventors attempted to capture the three-dimensional deformations of a single leaflet of a bioprosthetic mitral valve by employing the defocusing digital particle image velocimetry (DDPIV) principle in combination with trans-mitral flow mapping. In order to study the effect of trans-mitral flow on a mitral valve with deformable leaflets, tissue membrane deformation was measured within a left heart pulsed flow simulator. To measure deformation, the valve was marked with a number of dots, randomly distributed on the surface of the anterior leaflet (FIG. 1A). The transient motion of the dots was captured and their individual displacement and velocities were derived in a Lagrangian manner (FIG. 2A). The Lagrangian strain field (FIG. 2B) was computed by assuming that the thin anterior leaflet (leaflet thickness is much less than in-plane dimensions) was subjected to in-plane loading, with the shear deformation components in the thickness direction assumed to be negligible. Using the additional assumption of incompressibility to estimate $F_{33}$, the surface deformation gradient tensor (F) was computed at various times using measured leaflet motions (FIG. 1B). The corresponding Lagrangian strain tensor ($\epsilon$) is given by $$\varepsilon = \frac{1}{2}(F^T F - I) \qquad (1)$$

where $F^T$ is the transpose of deformation gradient tensor and I is the identity tensor. Though conceptually feasible, the DDPIV approach was hampered by technological limitations. For example, current DDPIV cameras cannot capture images faster than 30 fps which is far slower than the required number of frames for mapping the opening/closure of a heart valve within a cardiac cycle. A high-speed camera with the capturing capability of 250-1000 fps is required for accurate quantification of the leaflets' kinematic through a cardiac cycle (ranging from 30-100 beat per minute). In another study, a stereomicroscope system was developed and adapted to make quantitative, full-field, 3D surface displacement measurements on mouse aortas with micro-scale spatial resolution and nano-scale displacement accuracy. The approach overcomes the major limitation in prior work as the approach allows measurement of not only the surface profile (3D shape) but also the full 3D surface displacement fields and the complete surface strain tensor through differentiation of the 3D displacement field. Preliminary experimental results were reported when viewing a 0.40 mm diameter artery during cyclic pressurization, while also noting that the full-field measurements can be (a) used to identify local variations in material response or (b) integrated over an arbitrary length to obtain the average response in a specified region of the specimen.

In an effort to overcome the limitations of previous work including the limitations of DDPIV technique in assessment of leaflet dynamics, the present disclosure combines high-speed stereo imaging with digital image correlation to capture the transient three-dimensional deformations of heart valve's leaflets under physiologic flow conditions. Through direct, non-contacting measurements, the necessary response characteristics of a leaflet under physiologic pressure/flow conditions can be obtained. This information results in identifying the regions of a leaflet that are prone to damage within the period of valve function, and can lead to development of constitutive relationships for stress/strain in nonlinear membranes such as a tissue leaflet.

The present disclosure can be better understood with reference to the following examples.

EXAMPLES

Certain aspects of the present disclosure can be performed using the left heart pulsed flow simulator located at the Cardiovascular Engineering Laboratory in the Department of Mechanical Engineering at University of South Carolina. This system is modified to meet the measurement requirements of the imaging system developed in accordance with the present disclosure.

Figure 3:
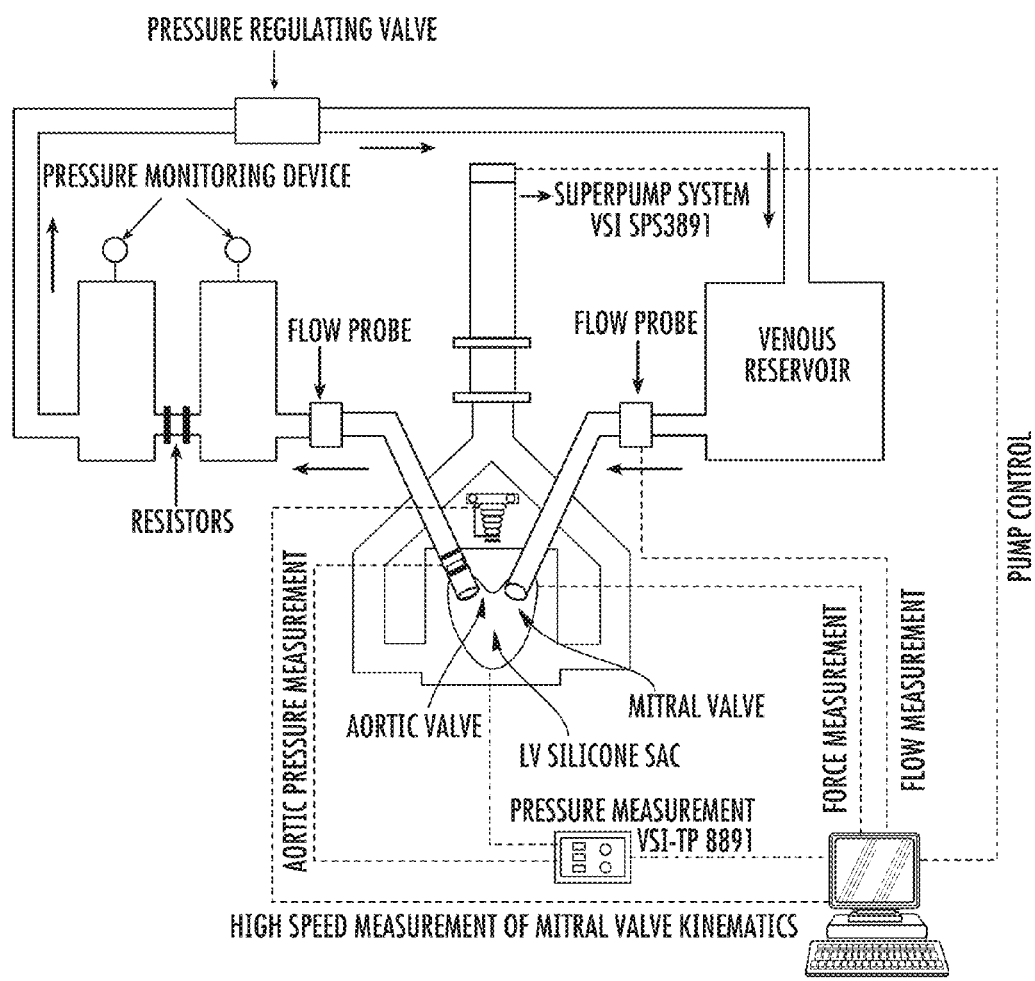
FIG. 3 illustrates schematics of the heart pulsed flow simulator system, in accordance with certain embodiments of the present disclosure.
Figure 4:
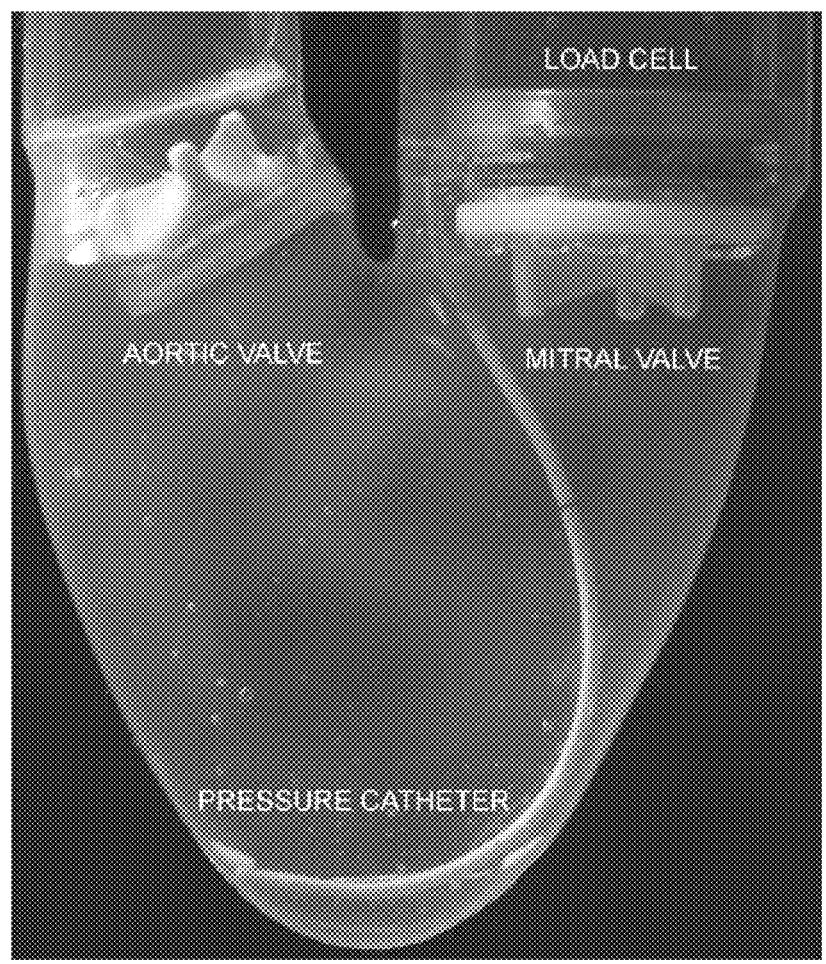
FIG. 4 illustrates a close-up view of the ventricular sac and its components, in accordance with certain embodiments of the present disclosure.

A schematic of the experimental setup will now be described. However, it should be appreciated that variations are contemplated to the setup as will be appreciated and understood to those in the art. Certain embodiments of the experimental setup are illustrated FIG. 3. The experimental setup is comprised of a left ventricular silicone sac activated by a suction pump that generates pressure drop outside the sac. High-speed cameras monitor mitral and aortic valve kinematics while a DAQ system records ventricular pressure, force exerted on the valves and the trans-mitral flow simultaneously. The system is comprised of a thin-wall ventricle, shaped according to molds in the systolic state, and made of transparent silicone rubber (FIG. 4). A 27 mm bioprosthetic mitral valve is securely positioned on a load cell that measures the total force exerted on the valve plane. A Swan-Ganz catheter is used to measure the LV pressure during cardiac cycles. A 23 mm bioprosthetic valve is used at the aortic position. The ventricular sac is suspended over the Plexiglas atrium (FIGS. 3 and 4) free-floating inside a rigid, water filled, cubic container. The container is made of Plexiglas to avoid optical distortion and is connected to a hydraulic pump system (Superpump system, VSI, SPS3891, Vivitro systems Inc., Victoria, BC, Canada). The pump is controlled by a customized MATLAB interface (MathWorks, Inc. Natick, Mass.) compatible with a National Instrument Data Acquisition device. The interface controls the motion of the pump's piston according to the predefined functions. The periodic, pulsatile flow in the circulatory system is generated as a response of the ventricular sac to the input waveforms provided by the pump. Appropriate water-glycerol mixture with viscous property similar to blood can be used as the circulating fluid. The waveforms are automatically adjusted based on the position, velocity and pressure feedbacks received by the power amplifier (VSI, SPA3891Z, Vivitro systems Inc., Victoria, BC, Canada).

Twenty Carpentier-Edwards' PERIMOUNT bioprosthetic heart valves (Edwards Lifesciences, Irvine, Calif.) are placed in mitral and aortic positions for measurement of their leaflet deformation under a variety of physiological flow during cardiac cycles. These heart valves are chosen due to their smooth, macroscopically homogenous leaflet material. The valves are marked with a number of water-resistant dye particles, randomly distributed on the surface of the leaflets (FIGS. 1A and 4).

The physiologic waveforms are generated and applied to imitate different conditions for the left ventricle (LV). The waveforms reproduce systolic ratios (SRs) of 35%, 40% and 50%, respectively, where systolic ratio (SR) is the fraction of time in a cardiac cycle that the LV is in systolic phase. The frequency of cycles is set to different values for each systolic ratio group ranging from 0.5 Hz to 1.67 Hz (0.5 Hz=30 bpm; 1.0 Hz=60 bpm; 1.2 Hz=72 bpm; and 1.67 Hz=100 bpm) reproducing the operational range of cardiac function. Each experiment is performed for 20 seconds to ensure the consistency and reproducibility of the results. To attain physiological conditions, the aortic afterload is set to fluctuate in the range of 80-120 mmHg (mean 100 mmHg)—similar to normal human aorta—during each cardiac cycle. The pressure at the aortic loop is measured by a pressure monitoring system during the experiment (Deltran DPT-400 Utah Medical Products, Inc, and VSI-TP8891 Vivitro Systems, Inc). The pressure information is used as an input to the feedback control system that adjusts the stroke ratio of the hydraulic pump system.

Figure 5:
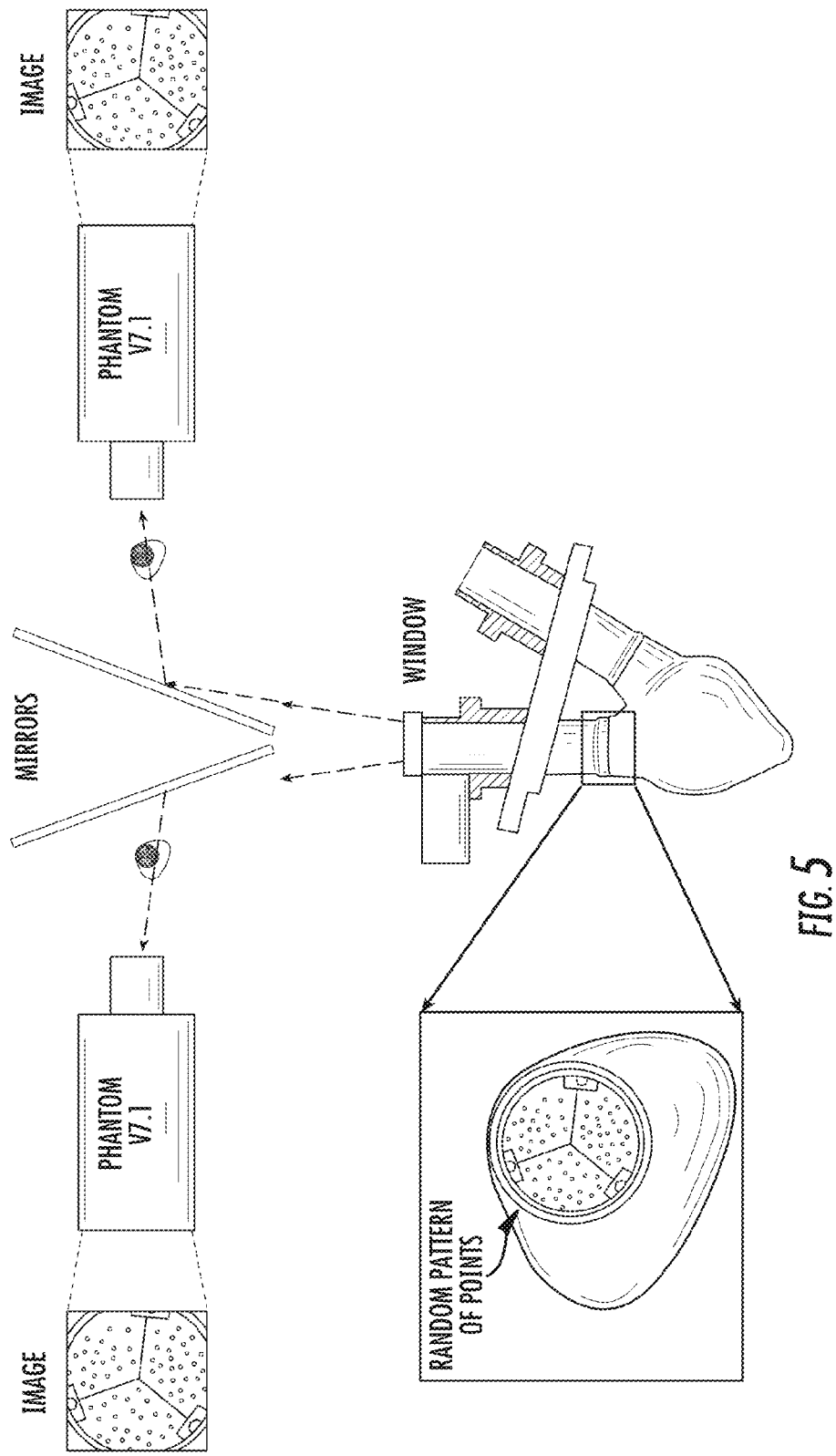
FIG. 5 illustrates a schematic of an integrated stereovision system viewing the heart simulator, in accordance with certain embodiments of the present disclosure.

High speed stereo imaging is combined with 3D digital image correlation to measure the transient three-dimensional deformations of valve leaflets under physiologic flow conditions. To achieve this objective, two hi-speed cameras (Phantom V7.1, Vision Research, Inc., Wayne, N.J.) are used for simultaneously acquiring high rate images of the valve leaflet from two different viewpoints. FIG. 5 shows an optical configuration for stereovision observation of a common region on the valve's leaflets. The schematic of a silicone sac model for LV with the mitral and aortic valves is clearly shown. The expanded view shows the coronal section of the aortic valve with the random pattern on its leaflets used to measure full-field 3D motions by digital image correlation method. Also shown is an optical window to view the leaflets during flow pulsation. Two high speed cameras are arranged to view the aortic valve. Lighting is input and images are output to the cameras using two mirrors. As shown in FIG. 5, the leaflet is observed through an optical window and images are digitally recorded via an 800×600 pixel sensor array (e.g. complementary metal oxide semiconductor (CMOS) for the V7.1 camera). Full-sensor images can be acquired at 4800 frames/sec, with increasing speed achievable by reducing spatial resolution (e.g., 60000 fps for 256×128 pixel array).

Figure 6:
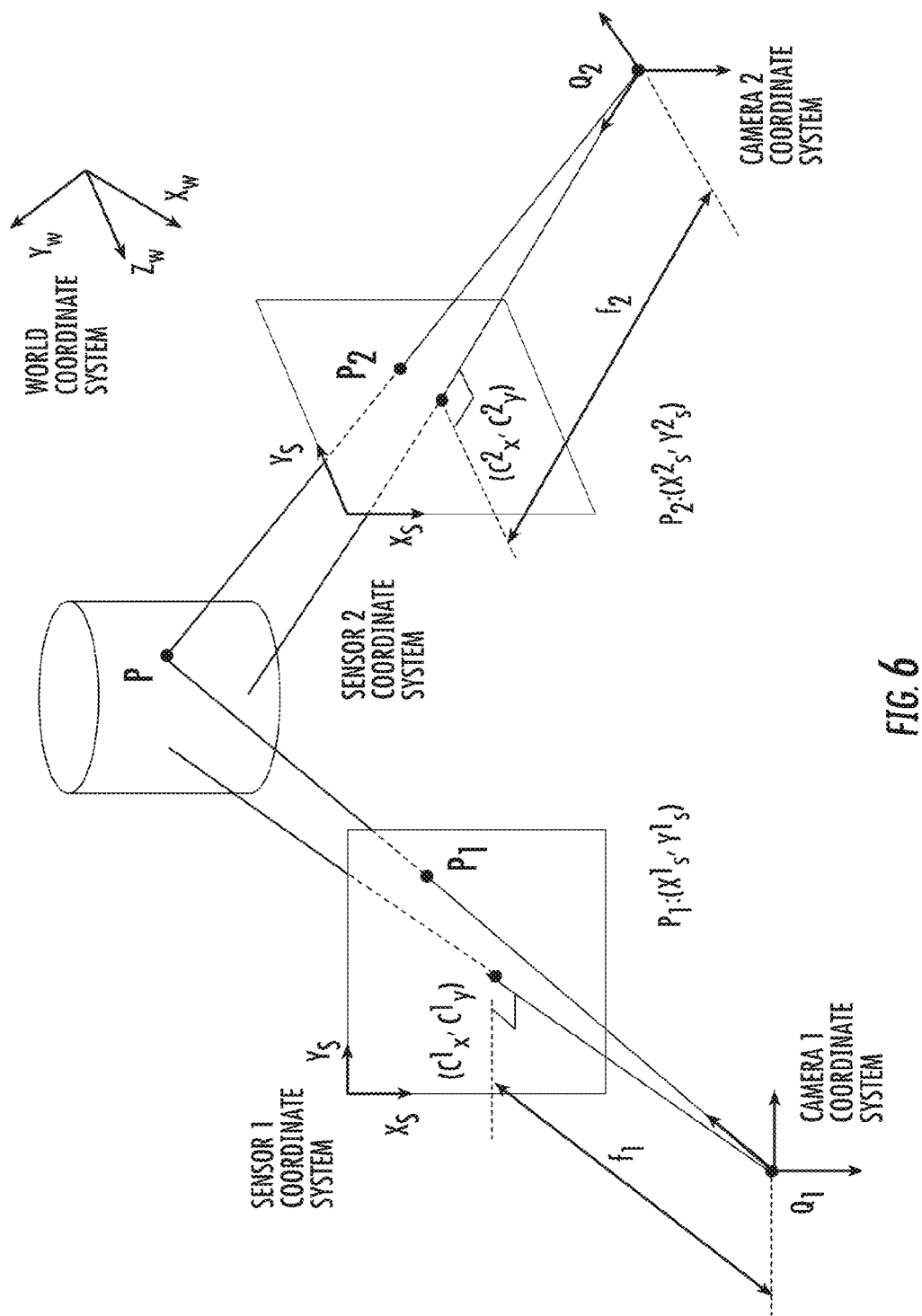
FIG. 6 illustrates a schematic of a two camera stereo-vision system viewing common point, P, in accordance with certain embodiments of the present disclosure.

FIG. 6 presents a schematic of the stereo-imaging process using two cameras. Sensor locations of point P when projected into cameras 1 and 2 are designated P1 and P2, respectively. Known sensor locations of point P in cameras 1 and 2 can be combined with calibrated camera parameters to optimally locate the true 3D position of P. Each camera converts the 3D position of a point P into a 2D sensor location. Inspection of the image process shown in FIG. 6 confirms that knowing the sensor location of an object point in one camera is not sufficient to locate uniquely the 3D position. For example, if only camera 1 is used, then any location along the line $Q_1$ to $P_1$ will still be imaged onto the same sensor location. To uniquely estimate the 3D position, sensor locations of a common point in two views are sufficient to extract the complete three-dimensional position information through optimal back-projection. To ensure that the same point is being viewed by both cameras, a matching process is performed to identify the same image subset (i.e., the same object region) in both camera views. Once the same image region is located in both views, the camera parameters within the mathematical imaging model are used to identify the rays $Q_1$ to $P_1$ and $Q_2$ to $P_2$. The optimal intersection location for these two rays identifies the 3D location of the common object point, P (FIG. 6).

When a pinhole camera model is used to describe the process of imaging a 3D point onto a 2D sensor plane, the equations can be written in the following form matrix form;

$$\alpha \begin{Bmatrix} x_s \\ y_s \\ 1 \end{Bmatrix} = \begin{bmatrix} & \vdots & & \vdots & \\ [K]\cdot[R] & \vdots & [K]\cdot\{t\} & \vdots & \\ & \vdots_{3\times3} & & \vdots_{3\times1} & \end{bmatrix} \cdot \begin{Bmatrix} X_w \\ Y_w \\ Z_w \\ 1 \end{Bmatrix} = [\Lambda]_{3\times4} \cdot \begin{Bmatrix} X_w \\ Y_w \\ Z_w \\ 1 \end{Bmatrix} \quad (2)$$

[R]=rotation tensor between world and camera systems
{t}=translation vector between origins of world and camera systems
[Λ]=[K]·[T]

$$[K] = [A]\cdot[P] = \begin{bmatrix} f\lambda_x & 0 & -\lambda_x \hat{c}_x \\ 0 & f\lambda_y & -\lambda_y \hat{c}_y \\ 0 & 0 & 1 \end{bmatrix} = \begin{bmatrix} f_x & 0 & c_x \\ 0 & f_y & c_y \\ 0 & 0 & 1 \end{bmatrix}$$

where ($c_x$, $c_y$) are the sensor plane locations of the image center (pixels); ($f\lambda_x$, $f\lambda_y$) is the product of the magnification factors (pixels/unit length) with the image distance from pinhole (length); ($X_w$, $Y_w$, $Z_w$) is the 3D position of the point of interest, [R] contains three independent components and defines the relative orientation of the camera and world systems; {t} contains three independent components and defines the translation of the two systems. In this form, there are ten parameters to relate 3D positions to 2D sensor positions. If radial lens distortions are significant, then an additional parameter, κ, is included to correct the image positions, resulting in eleven parameters to be determined.

Digital image correlation is used to identify matching subset locations in both cameras; each pair of matching sensor locations corresponds to the same 3D point in space. The sensor locations are placed in Equation (2) for each camera, resulting in 4 equations for the 3D position; ($X_w$, $Y_w$, $Z_w$), of the corresponding object point. The over-determined set is solved using a minimization process in the sensor plane to define the best estimate for the common object point location.

The process is repeated for subsets throughout the image, resulting in a dense set of 3D positions that represent the object.

Figure 7:
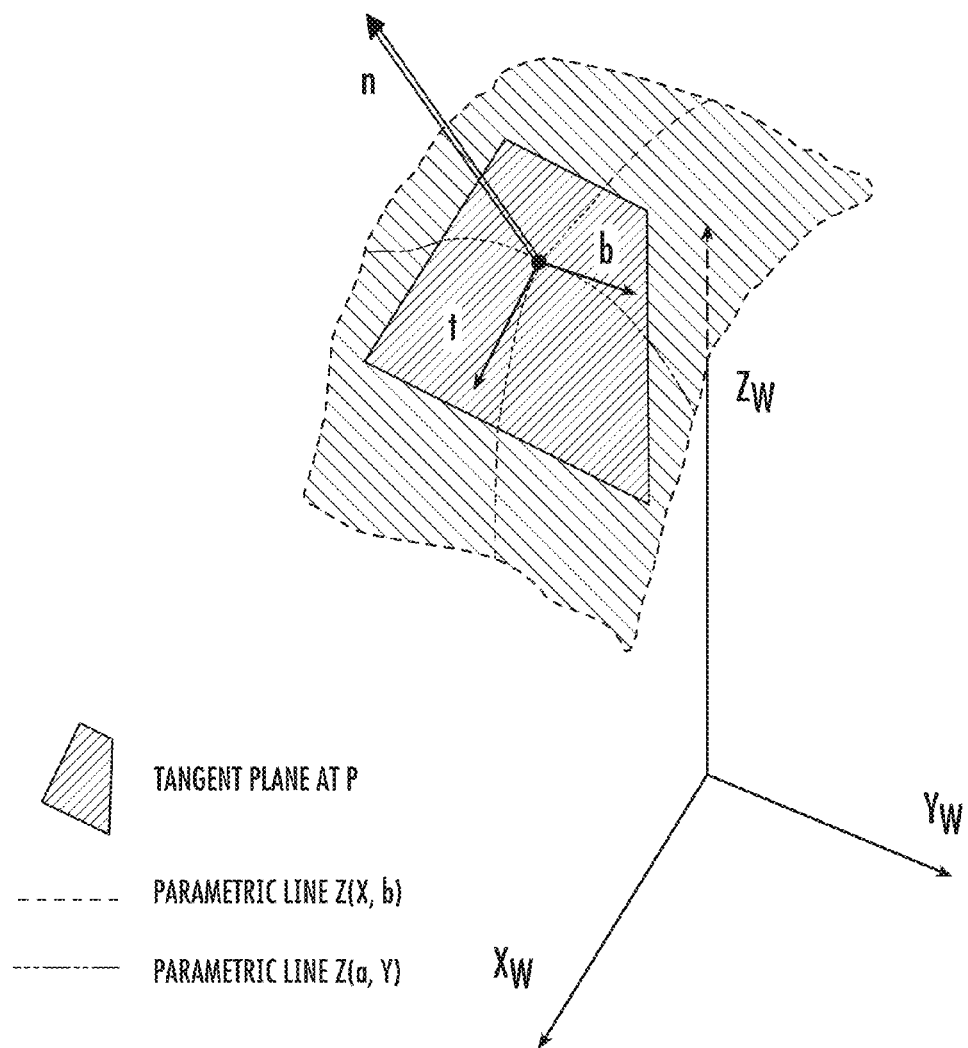
FIG. 7 illustrates a schematic of focal planar surface fit for strain estimation at surface points, in accordance with certain embodiments of the present disclosure.

Once a dense set of 3D positions is obtained at each time of interest, the data can be processed to define the complete surface strain field at each point on the leaflet. First, as shown in FIG. 7, a plane is fitted locally to define a tangent-normal-binormal system at each point P, where (t(P), b(P)) define orthogonal in-plane directions and n(P) defines the local normal. Second, the rigid body rotation tensor transforming the global into the local system, $[R_L]$, is determined. Third, a least squares quadratic fit is performed for each displacement component and the partial derivatives with respect to the world coordinate directions, ($X_1$, $X_2$, $X_3$), are obtained at the center point. Fourth, the derivatives are used to obtain the in the following component form for the Lagrangian strain tensor; the form used is invariant with rigid body motion so that overall rotation of the leaflet during pressure cycling will not affect the strain measurements.

$$E_{11} = \frac{\partial d_1}{\partial X_1} + \frac{1}{2}\left[\left(\frac{\partial d_1}{\partial X_1}\right)^2 + \left(\frac{\partial d_2}{\partial X_1}\right)^2 + \left(\frac{\partial d_3}{\partial X_1}\right)^2\right] \quad (3)$$

$$E_{22} = \frac{\partial d_2}{\partial X_2} + \frac{1}{2}\left[\left(\frac{\partial d_1}{\partial X_2}\right)^2 + \left(\frac{\partial d_2}{\partial X_2}\right)^2 + \left(\frac{\partial d_3}{\partial X_2}\right)^2\right]$$

$$E_{33} = \frac{\partial d_3}{\partial X_3} + \frac{1}{2}\left[\left(\frac{\partial d_1}{\partial X_3}\right)^2 + \left(\frac{\partial d_2}{\partial X_3}\right)^2 + \left(\frac{\partial d_3}{\partial X_3}\right)^2\right]$$

$$E_{12} = \frac{1}{2}\left(\frac{\partial d_1}{\partial X_2} + \frac{\partial d_2}{\partial X_1}\right) + \frac{1}{2}\left[\left(\frac{\partial d_1}{\partial X_1}\frac{\partial d_1}{\partial X_2}\right) + \left(\frac{\partial d_2}{\partial X_1}\frac{\partial d_2}{\partial X_2}\right) + \left(\frac{\partial d_3}{\partial X_1}\frac{\partial d_3}{\partial X_2}\right)\right]$$

$$E_{23} = \frac{1}{2}\left(\frac{\partial d_2}{\partial X_3} + \frac{\partial d_3}{\partial X_2}\right) + \frac{1}{2}\left[\left(\frac{\partial d_1}{\partial X_2}\frac{\partial d_1}{\partial X_3}\right) + \left(\frac{\partial d_2}{\partial X_2}\frac{\partial d_2}{\partial X_3}\right) + \left(\frac{\partial d_3}{\partial X_2}\frac{\partial d_3}{\partial X_3}\right)\right]$$

$$E_{31} = \frac{1}{2}\left(\frac{\partial d_3}{\partial X_1} + \frac{\partial d_1}{\partial X_3}\right) + \frac{1}{2}\left[\left(\frac{\partial d_1}{\partial X_3}\frac{\partial d_1}{\partial X_1}\right) + \left(\frac{\partial d_2}{\partial X_3}\frac{\partial d_2}{\partial X_1}\right) + \left(\frac{\partial d_3}{\partial X_3}\frac{\partial d_3}{\partial X_1}\right)\right]$$

Equation (3) gives the strains at the center-point of the region in FIG. 7. To determine the strains in the plane defined by (t, b), directions (I, II, III) correspond to the orthogonal directions (t, b, n). Then, the appropriate tensor transformation can be performed to obtain strains within the specimen surface plane:

$$E_{II}(P) = R_{I\alpha}(P)\cdot R_{I\beta}(P)\cdot E_{\alpha\beta}(P)$$

$$E_{III}(P) = R_{I\alpha}(P)\cdot R_{II\beta}(P)\cdot E_{\alpha\beta}(P)$$

$$E_{IIII}(P) = R_{II\alpha}(P)\cdot R_{II\beta}(P)\cdot E_{\alpha\beta}(P) \quad (4)$$

The process outlined above is repeated at each point to obtain the Lagrangian strain field experienced by the leaflet.

The primary issue in the vision studies is the effect of refraction at the air-Plexiglas or Plexiglas-fluid interface on the stereo-measurements. To perform accurate metrology on a submerged specimen using optical images, the "air" calibration process can be modified to include the effect of both the air-glass and glass-fluid interfaces on "system" calibration. Preliminary simulation results with and without considering the effects of refraction are presented here.

Figure 8:
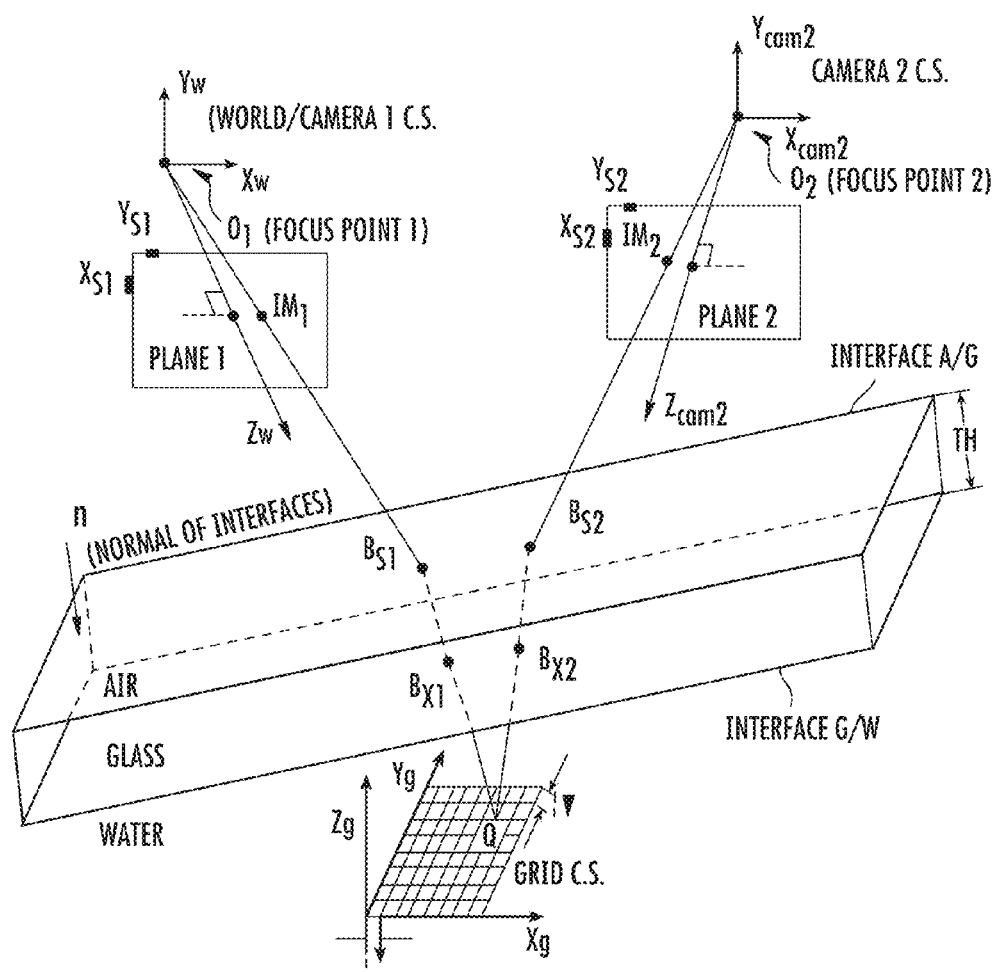
FIG. 8 illustrates a schematic of stereo-imaging process with air-glass and glass-fluid interfaces, in accordance with certain embodiments of the present disclosure.

As shown in FIG. 5, the initial concept for performing submerged imaging of the BHV during pressure cycling is to use stationary cameras, stationary mirrors, stationary window for viewing leaflet and fluid-filled chamber. To demonstrate the feasibility of performing the measurements with optimal accuracy, basic theoretical studies and simulations for the idealized setup have been performed as shown in FIG. 8. Simulations indicate that a calibration method can be developed to calibrate each camera using standard air calibration as would be known in the art, and additional parameters that locate an air-water and/or air-glass interface to define the orientation and position of the interface(s).

Using a calibrated stereo camera system with interface parameters, preliminary studies performed show that using air calibration parameters without considering refraction at the fluid-air interface will result in strain errors >0.05 when the leaflet undergoes 30° rotation. However, by including parameters to locate the interface, strain errors are less than 0.002 and generally independent of the angle of rotation of the leaflet, assuming that cross-camera image correlation shown in FIG. 8 can be performed. Based on the results, it is clear that the effect of refraction should be included in the calibration process to obtain accurate strain values.

In certain aspects of the present disclosure, the heart pulsed flow simulator can be modified to incorporate an appropriate transparent viewing portal for the stereo-vision system. Since most of the components of this system are modular and can be replaced, the modification envisioned in FIG. 5 can easily be accommodated. Construction of a combined mirror-camera system for attachment to the flow loop and experiments to demonstrate calibration procedures are also readily adaptable for BHV measurements. Once the modifications have been completed and a calibration approach demonstrated successfully, preliminary validation measurement studies within the flow loop can be performed to obtain quantitative error estimates. To demonstrate the feasibility of performing the measurements with optimal accuracy, basic theoretical studies and simulations have been performed for the idealized setup shown in FIG. 8. Such a technique will be used to calibrate each camera using standard air calibration as discussed before. Such a methodology will also be used to locate an air-water and/or air-Plexiglas interface and to obtain the orientation and position of the interface(s) relative to the calibrated cameras. Once full calibration is completed, the combined vision system with interface parameters can be used to measure the 3D motions of an object submerged in the fluid at variable depths and subjected to a range of rigid body rotations. Here, the measured surface strain field will provide a metric for the accuracy of the corrected 3D position measurements.

Figure 9:
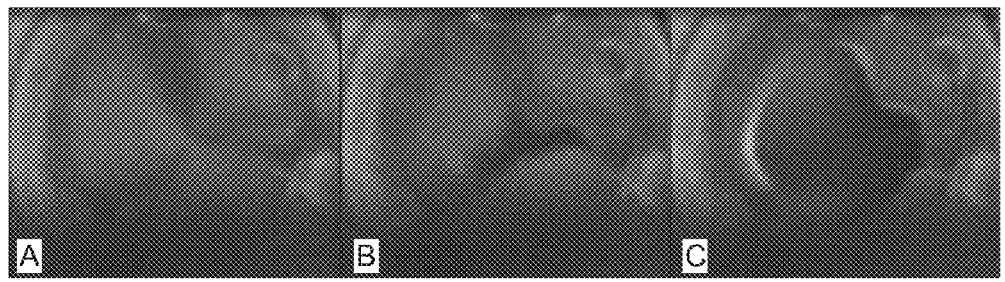
FIG. 9 illustrates the full view of tri-leaflet aortic valve opening wherein (A) the valve is fully closed; (B) the valve is opening, and (C) the valve is fully open, in accordance with certain embodiments of the present disclosure.

Obtaining the tri-leaflet deformation scheme during valve opening and closure (FIG. 9) is also contemplated by the present disclosure. FIG. 9 illustrates the full view of tri-leaflet aortic valve opening. These images are taken with a high-speed camera (Redlake Inc, Tallahassee, Fla.) with low resolution (250×250). The aortic valve is viewed from top where the camera was positioned parallel to the valve. First, the stereovision system with mirrors will be integrated into the flow loop system. Second, methods in accordance with the present disclosure are utilized to allow for ease in calibration of the imaging system after integration into the flow loop. Third, calibration and preliminary measurements are obtained to demonstrate that the system is fully functional after integration.

Figure 10:
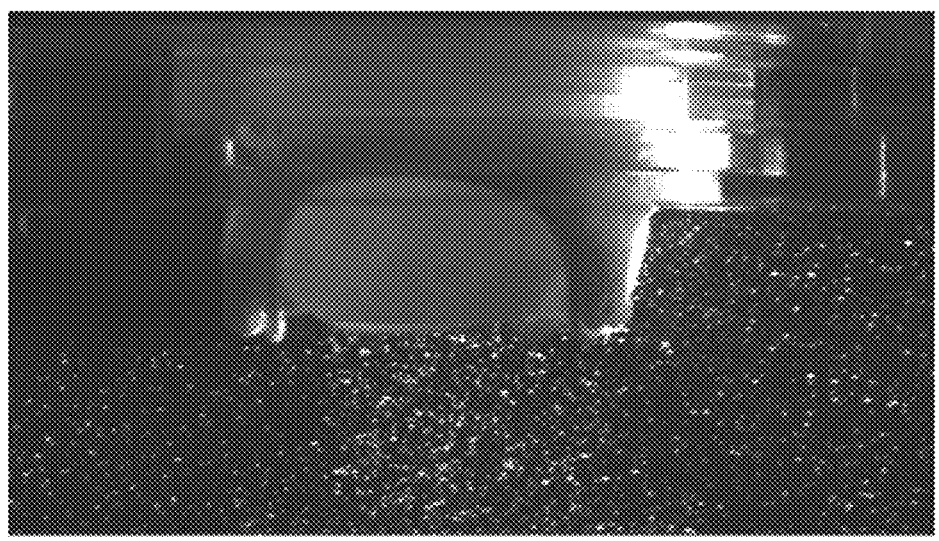
FIG. 10 illustrates a close-up side view of the anterior leaflet of a tri-leaflet bioprosthetic heart valve at mitral position (image taken using a high-resolution monochrome CCD digital camera, 30 fps, 768×480; TM-9701, PULNiX America, Inc.), in accordance with certain embodiments of the present disclosure.

After completing this phase, initial measurements of transient deformations in both aortic and mitral valves can be obtained. First, the afterload and preload are adjusted to the desired physiologic conditions. Next, the cameras are synchronized with the pulsatile pump system for correlating images with specific times-frame in the cardiac cycle. For the aortic valve, the mirrors will be installed distal to the valve, properly inclined with respect to the aortic housing (FIG. 5). For the mitral valve (FIGS. 4 and 9), the required mirrors will be installed distal to the valve itself within the LV silicone sac. The mitral setup may require modification to ensure that stable images are acquired throughout the cardiac cycle. The leaflets' response will be studied be under different systolic ratios and different heart rates (30 bpm to 100 bpm), see FIG. 10.

In certain embodiments of the present disclosure, the single leaflet deformation of the previously measured tri-leaflet valve is measured. Having the same experimental condition, the deformation of each leaflet will be independently measured using 3D digital image correlation combined with high-speed stereo imaging. To measure the deformation of an aortic valve, the aortic loop component is modified, replacing a cylindrical section with a prism-shape container where the prism's surfaces are parallel with the valve's leaflets. The afterload will be adjusted to the values previously discussed herein to maintain the same experimental conditions. This configuration will provide an excellent field of view to capture the deformation of each leaflet. As noted previously, the vision-based measurement is challenging for the valve placed at the mitral position. Preliminary concepts envision an apparatus comprising two spatially adjustable mirrors being placed around the sac inside the cubic Plexiglas chamber. This apparatus can rotate around the valve to provide an appropriate field of view for each leaflet. The imaged is captured by high-speed cameras outside the cubic chamber, considering the refraction coefficients of Plexiglas, water and silicone sac.

The primary data will be the transient shape and displacement fields for the leaflets on the aortic and mitral valves, along with the corresponding LV pressure measurements (P). The shape and deformation data obtained for each point on the leaflet will be processed to generate full-field measurements for; (1) displacement vector $\underline{d}(P, t)$, (2) velocity $v(P, t)$ and acceleration vectors $\underline{a}(P, t)$, (3) strain tensor $\underline{E}(P, t)$ and (4) strain rate metrics $\underline{\dot{E}}(P, t)$. It is noted that the data can be analyzed to obtain either Lagrangian or Eulerian metrics, with Lagrangian metrics typically preferred in many applications where the deformations of a specific material point are of interest. The measurements will be analyzed in a variety of ways to elucidate trends or specific features in the leaflet response. For example, a leaflet deformation/strain map as function of time during a complete cardiac cycle is generally of interest, especially when seeking information regarding high and low strain regions and their evolution. The measured response of the leaflet throughout a cardiac cycle offers opportunities for analytical comparisons. Following the general approach further described herein, the measured transient motions and surface deformations on the leaflet under a variety of physiologic loading conditions provides opportunities for relating finite element analysis predictions to quantitative measurements. Furthermore, the data also suggests the potential for use of inverse methods to estimate the continuum-type constitutive response of the leaflet, provided that the loading conditions (e.g., surface interactions) are reasonably well known.

Accurate simulations to predict the measured motions and deformations of a leaflet require knowledge of the boundary conditions (e.g., applied pressure, local fixity of leaflet regions) together with the constitutive properties of the material. Experimentally, flow conditions can be monitored to provide reasonable fluid pressure estimates. However, even if the pressure distribution on the leaflet is known with acceptable accuracy, it is unlikely that measured surface deformations and motions will be sufficient to develop an inverse procedure for estimating a reasonable number of leaflet material properties.

As an example, simple pressurization of a membrane has previously been employed in an effort to extract four distinct material properties using selected surface motions for comparison. Noting that the results of the optimization procedures described a material parameter set capturing the experimental data in an objective best sense, the results they observed were non-unique in general, requiring additional measurements to estimate all four parameters. A similar result was found when combining (a) strain measurements during pressurization of a vessel and (b) simple axial loading of the vessel, confirming that additional experimental measurements are needed to quantify specific constitutive parameters (e.g. the through-thickness stiffness parameter).

In accordance with the present disclosure, an experimental approach to quantify leaflet constitutive properties using the non-contacting vision method together with biaxial, tension and tension/torsion loading is contemplated. In this regard, a biaxial loading apparatus, a tension-torsion loading system (Bose, Elf 3200 tension-torsion system), a miniature uniaxial loading system (Fullam) and a Plexiglas environmental chamber for mechanical loading in a submerged environment, can be utilized. In particular, methodologies can be employed with appropriate material models for the leaflet to quantify constitutive parameters for the leaflet, as well as other membrane materials, through modification of existing facilities. Results from the experimental studies (e.g., mechanical loading, microstructural characterization) can be combined with appropriate simulation methods and reasonable material models (e.g. Mooney-Rivlin, Ogden and Arruda-Boyce) to estimate leaflet constitutive properties. These results can be employed in simulations of the in-vivo motion to assess the quality of the predictions and provide additional validation data for the constitutive model and parameters.

The results of the present disclosure introduce a new methodology to identify the presence of currently undetectable structural defects in bioprosthetic heart valves. The methods described herein can lead to improved quality and structural durability of these valves, while preventing the release of defective ones for clinical use. Additionally, the results obtained herein have the potential to impact the industry to improve the current valve design and to initiate novel technologies for assessment of percutaneous heart valve systems. The proposed methodology is not only adaptable for conventional surgically implantable valves, but also can be used to evaluate novel percutaneous valve devices. This approach can be applied for validation of new design concepts as well as screening of novel heart valve materials, thereby accelerating the development of the next generation of heart valves. In addition, successful implementation of a non-contacting, image-based measurement method for measuring 3D strains can be employed to extend the method to use ultrasonic waves instead of light to quantify the 3D strain field of a natural heart valve within the heart itself; this approach has the potential for use in cardiac studies. The method could result in non-invasive quantification of natural heart valves function which is considered a remarkable step in early diagnosis of valvular heart diseases.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure.

What is claimed is:

1. A method for deformation mapping of a tissue comprising:
utilizing a device to measure transient three-dimensional deformations in a tissue sample comprising a heart valve under physiologic flow conditions which replicate valve opening and closure, the device comprising a non-contacting, high-speed stereo imaging apparatus, a pulsatile pump system configured to provide periodic pulsatile flow of fluid through the heart valve, and a mechanism for digital image correlation, wherein the pulsatile pump system is configured to operate in synchronization with the high speed stereo imaging apparatus; and
identifying regions of the tissue that are prone to damage based upon the deformations.

2. The method as in claim 1, wherein the heart valve comprises a bioprosthetic heart valve.

3. The method as in claim 1, wherein the high speed stereo imaging apparatus comprises two cameras.

4. The method as in claim 1, further comprising marking the surface of the tissue with particles.

5. The method as in claim 4, wherein the particles comprise water-resistant dye particles.

6. A device for deformation mapping a tissue comprising:
a non-contacting, high-speed stereo imaging apparatus, a pulsatile pump system, and a mechanism for digital image correlation, wherein the high speed stereo imaging apparatus and the mechanism for digital image correlation are configured to measure transient three-dimensional deformations in a tissue sample comprising a heart valve under physiologic flow conditions which replicate valve opening and closure and identify regions of the tissue that are prone to damage based upon the deformations, and wherein the pulsatile pump system is configured to provide periodic pulsatile flow of fluid through the heart valve and operate in synchronization with the high speed stereo imaging apparatus.

7. The device of claim 6, wherein the high speed stereo imaging apparatus comprises one or more mirrors.

8. The device of claim 6, wherein the high speed stereo imaging apparatus comprises two cameras.

9. The device of claim 8, wherein the cameras are high speed cameras.

10. The device of claim 9, wherein the high speed stereo imaging apparatus comprises an optical window, the tissue sample being capable of being observed through an optical window by the high speed cameras.

* * * * *